United States Patent [19]

Tanaka et al.

[11] Patent Number: 5,631,213
[45] Date of Patent: May 20, 1997

[54] PROCESS FOR PRODUCING MOLYBDENUM OXYSULFIDE DITHIOCARBAMATE

[75] Inventors: Noriyoshi Tanaka; Aritoshi Fukushima; Yukio Tatsumi; Kazuhisa Morita; Yoko Saito, all of Tokyo, Japan

[73] Assignee: Asahi Denka Kogyo K. K., Tokyo, Japan

[21] Appl. No.: 597,898

[22] Filed: Feb. 6, 1996

[30] Foreign Application Priority Data

Feb. 15, 1995 [JP] Japan ................... 7-026815

[51] Int. Cl.$^6$ ........................... C10M 115/00; C07F 1/00
[52] U.S. Cl. ........................ 508/363; 508/364; 508/365; 556/38; 556/39
[58] Field of Search ........................ 508/363; 556/38, 556/39

[56] References Cited

U.S. PATENT DOCUMENTS

| | | | |
|---|---|---|---|
| 3,356,702 | 12/1967 | Farmer et al. | 556/38 |
| 4,098,705 | 7/1978 | Sakurai et al. | 252/33.6 |
| 4,588,829 | 5/1986 | Pan et al. | 556/38 |
| 4,681,957 | 7/1987 | Singhal et al. | 556/38 |
| 4,683,316 | 7/1987 | Singhal et al. | 556/38 |
| 4,846,983 | 7/1989 | Ward, Jr. | 252/33.6 |
| 5,445,749 | 8/1995 | Hong | 252/33.6 |
| 5,462,683 | 10/1995 | Kinoshita et al. | 252/25 |
| 5,487,837 | 1/1996 | Ozaki et al. | 252/25 |
| 5,494,608 | 2/1996 | Kamakura et al. | 252/42.7 |

FOREIGN PATENT DOCUMENTS

| | | |
|---|---|---|
| 45-24562 | 8/1970 | Japan . |
| 48-56202 | 8/1973 | Japan . |
| 52-19629 | 2/1977 | Japan . |
| 52-106824 | 9/1977 | Japan . |
| 4-182494 | 6/1992 | Japan . |

*Primary Examiner*—Ellen M. McAvoy
*Attorney, Agent, or Firm*—Oblon, Spivak, McClelland, Maier & Neustadt, P.C.

[57] ABSTRACT

A process for producing molybdenum oxysulfide dithiocarbamate (MoDTC) by reacting [A] an aqueous solution or suspension prepared by reacting (a) a compound having hexavalent molybdenum, with (b) an alkali hydrogensulfide or an alkali sulfide, [B] a carbon disulfide, [C] a secondary amine and [D] a mineral acid, wherein [E] a reducing agent is added and reacted at any stage, and a lubricating oil composition containing the compound obtained according to said process. MoDTC can be efficiently produced in high yields by using a hexavalent molybdenum compound as a starting material, and the produced MoDTC has low corrosive action, excellent wear characteristics and excellent lubricating properties.

14 Claims, No Drawings

PROCESS FOR PRODUCING MOLYBDENUM OXYSULFIDE DITHIOCARBAMATE

BACKGROUND OF THE INVENTION

1. Field of the Invention

The present invention relates to a process for producing molybdenum oxysulfide dithiocarbamate (hereinafter referred to as MoDTC) and a lubricant composition containing the MoDTC produced by said production process. More specifically, the present invention relates to a process for producing MoDTC which exhibits low corrosive action and has excellent lubricating properties, efficiently in high yields, and a lubricant composition containing said MoDTC.

2. Description of the Related Art

Currently, as automobiles have increased in performance and become high-powered, the conditions of use for engine oils have become more and more severe. Particularly since the reduction of fuel consumption has been gaining attention as an important environmental matter, engine oil viscosity has been reduced, large amounts of friction modifiers have been used, or the quality of friction modifiers have been improved, in order to enhance fuel consumption.

Under such conditions, the use of MoDTC showing excellent friction modifier properties and anti-wear characteristics has become a focus of attention.

Japanese Patent Publication No. 45-24562 discloses a method in which a compound represented by the following general formula:

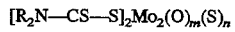

(wherein m+n=4, m=2.35–3, n=1.65–1, and R represents a hydrocarbyl group having 1 to 24 carbon atoms) can be obtained from a secondary amine, carbon disulfide and molybdenum trioxide.

Also, Japanese Patent Laid-Open No. 48-56202 discloses a method in which a compound represented by the following general formula:

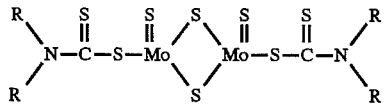

(wherein R is an alkyl group) can be produced by reacting the product given by the method of Japanese Patent Publication No. 45-24562 described above with phosphorus pentasulfide.

However, the compound disclosed in the above-mentioned Japanese Patent Publication No. 45-24562 shows inferior heat resistance and the compound disclosed in the above-mentioned Japanese Patent Laid-Open No. 48-56202 is corrosive to copper plates, thus the use of those compounds has been limited.

In order to improve such drawbacks, Japanese Patent Laid-Open Nos. 52-19629 and 52-106824 disclose methods to produce a compound represented by the following general formula:

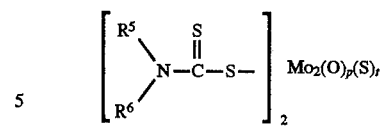

(wherein $R^5$ and $R^6$ are independently hydrocarbyl groups having 1 to 24 carbon atoms, p is a number from 0.5 to 2.3, t is a number from 3.5 to 1.7 and p+t=4) by reacting carbon disulfide with a secondary amine in an aqueous solution or suspension containing molybdenum trioxide or an alkali metal salt or an ammonium salt of molybdic acid and an alkali hydrogensulfide or an alkali sulfide in a molar ratio of 1:0.05–4.

Also Japanese Patent Laid-Open No. 4-182494 discloses a method by which a compound represented by the following general formula:

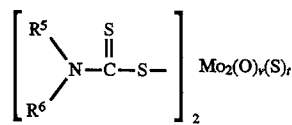

(wherein $R^5$ and $R^6$ are independently hydrocarbyl groups having 1 to 24 carbon atoms, v is a number from 0.5 to 2.3, y is a number from 3.5 to 1.7, and v+y=4) can be produced by reacting carbon disulfide and a secondary amine with an aqueous solution having pH of 8.5–11, wherein molybdenum trioxide, or an alkali metal salt or an ammonium salt of molybdic acid, and an alkali hydrogensulfide or an alkali sulfide are blended.

The methods disclosed in the above-mentioned Japanese Patent Laid-Open No. 52-19629, Japanese Patent Laid-Open No. 52-106824, and Japanese Patent Laid-Open No. 4-182494, are for obtaining MoDTC which has nearly the same skeletal structure as the end-product, by using a hexavalent molybdenum compound as a starting material. However, the yields remain low, and the purity of the product is low as well, thus the product has poor lubricity.

SUMMARY OF THE INVENTION

An object of the present invention is to solve the above-mentioned conventional problems and to provide a process for producing molybdenum oxysulfide dithiocarbamate in which a hexavalent molybdenum compound is used as a starting material, and MoDTC having low corrosive action, excellent wear characteristics and excellent lubricating properties which can be efficiently produced in high yields.

Another object of the present invention is to provide a lubricant composition containing MoDTC which exhibits little corrosive action, excellent wear characteristics and excellent lubricity.

The present inventors have carried out an extensive research on a process for producing molybdenum oxysulfide dithiocarbamate which exhibits little corrosive action and excellent wear characteristics and lubricity, using a hexavalent molybdenum compound as the starting material. As a result of the research, they have found a process for producing high purity MoDTC, efficiently in high yields, and completed the present invention.

Accordingly, an object of the present invention is to provide a process for producing molybdenum oxysulfide dithiocarbamate which is represented by the following general formula (1):

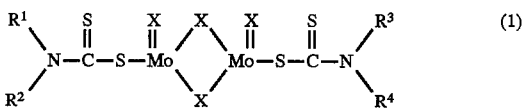

(1)

(wherein $R^1$, $R^2$, $R^3$ and $R^4$ are hydrocarbyl groups which may contain oxygen, and X is sulfur atom or oxygen atom) by reacting

[A] an aqueous solution or suspension prepared by reacting (a) a compound having hexavalent molybdenum, with (b) an alkali hydrogensulfide or an alkali sulfide,

[B] a carbon disulfide,

[C] a secondary amine and

[D] a mineral acid, wherein

[E] a reducing agent is added and reacted at any stage.

Another object of the present invention is to provide said production process wherein the blending ratio of components [A], [B], [C] and [D] are such that the amount of component [B] is 0.9–2 moles, that of component [C] is 0.9–2 moles to 1 mole of the hexavalent molybdenum atom contained in component [A], and that d, which is the equivalent weight of component [D] to be added when the alkali equivalent of component [A] is defined as 1, is within the range satisfying the following equation (2), when R' is less than 32, $$1-[R'/4)+1]\times 1/10 \leq d \leq 1 \quad (2)$$

and d is within the range satisfying the following equation (3) when R' is equal to or more than 32, $$0.1 \leq d \leq 10/[(R'/4)+2] \quad (3)$$

(wherein R' is the total number of carbon atoms contained in $R^1$, $R^2$, $R^3$ and $R^4$).

Still another object of the present invention is to provide said production process wherein (b) the alkali hydrogensulfide or alkali sulfide of 0.01–4 moles is reacted with 1 mole of molybdenum atom contained in (a) the compound having hexavalent molybdenum.

A further object of the present invention is to provide said production process wherein the blending ratio of [E] the reducing agent is 0.01–4 moles to 1 of the molybdenum atom contained in [A].

A still further object of the present invention is to provide said production process wherein [E] the reducing agent is added during and/or after the reaction between (a) the compound having hexavalent molybdenum and (b) the alkali hydrogensulfide or alkali sulfide.

A yet still further object of the present invention is to provide said production process wherein [E] the reducing agent is one or more compounds selected from the group consisting of a hydride, an alkali metal salt of dithionous acid, sulfurous acid or thiosulfuric acid, an alkaline earth metal salt of dithionous acid, sulfurous acid or thiosulfuric acid, a sulfur compound, a reducing sugar, aldehydes and a reducing acid.

A yet still further object of the present invention is to provide said production process wherein $1.0 \leq m \leq 3.5$, when the composition of the total of all X's in the general formula (1) is given as $S_mO_n$.

A yet still further object of the present invention is to provide a lubricant composition containing molybdenum oxysulfide dithiocarbamate which is produced by the above-mentioned production process.

A yet still further object of the present invention is to provide said lubricant composition which contains zinc dithiophosphate.

DETAILED DESCRIPTION OF THE INVENTION

The present invention will be further explained in detail.

The structure of the above-mentioned general formula (1) is given for convenience' sake and it has been made clear that scientifically the structure can be represented by the following general formula (4).

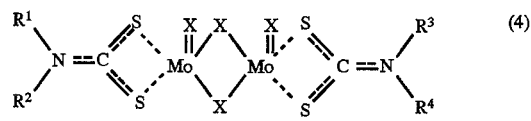

(4)

N—C—SS bonds are conjugated among 4 atoms in the dithiocarbamic acid moiety, which is negatively monovalent as a whole. $Mo_2X_4$ is positively divalent as a whole. Accordingly, it can be said that MoDTC is a salt formed between dithiocarbamic acid and $Mo_2X_4$.

Component [A]

In the component [A] according to the process of the present invention, (a) a compound having hexavalent molybdenum [hereinafter referred to as a hexavalent molybdenum compound (a)] is not particularly limited, however, inorganic compounds such as metal salt of molybdic acid, ammonium salt of molybdic acid and molybdenum trioxide (molybdic anhydride) are preferable since they are solid and easily used for production. As a metal salt of molybdic acid, preferably used are alkali metal salts such as sodium molybdate and potassium molybdate.

In the component [A] according to the process of the present invention, illustrative examples of (b) an alkali hydrogensulfide include sodium hydrogensulfide, potassium hydrogensulfide and the like. The alkali hydrogen sulfide can be used either in the form of a flake or an aqueous solution, however, when (a) the hexavalent molybdenum compound is solid, as it is hard to carry out solid-solid reaction, an aqueous alkali hydrogensulfide solution, which is liquid, is preferable. Apart from that, illustrative examples of (b) the alkali sulfide include sodium sulfide, potassium sulfide, ammonium sulfide and the like. In addition, aqueous solutions thereof or an aqueous alkali sulfide solution prepared by introducing a sulfurizing gas into an aqueous alkali hydroxide solution can be used as well.

In the process for preparation of an aqueous solution or aqueous suspension (hereinafter referred to as aqueous suspension etc.) by reacting (a) a hexavalent molybdenum compound with (b) an alkali hydrogen sulfide or alkali sulfide (hereinafter, referred to as (b) an alkali hydrogensulfide etc.), they must be reacted at least partially, preferably equal to or more than 50 mole %, and more preferably equal to or more than 80 mole %, prior to the reaction with [B] carbon disulfide, [C] a secondary amine, and [D] a mineral acid. If the reaction carried out is below 50%, a large amount of by-products may be undesirably produced to give bad effects on the purity and the yield of MoDTC, which is the end-product.

Since the reacting ratio between (a) a hexavalent molybdenum compound and (b) an alkali hydrogen sulfide etc. is a factor for determination of the composition of the X's in formula (1), by controlling the reacting ratio appropriately, the composition of X's can be so adjusted that the MoDTC may be suitable for the use application and the working environment. When the amount of (b) an alkali hydrogensulfide etc. to be used is large, the composition of X's becomes sulfur-rich, and when the amount of (b) an alkali hydrogensulfide etc. to be used is little, the composition of X's becomes oxygen-rich. Accordingly, the reaction ratio between (a) a hexavalent molybdenum compound and (b) an alkali hydrogensulfide etc. is not particularly limited, but it is preferable that the ratio of (b) the alkali hydrogensulfide etc. is 0.01–4 moles, preferably 1–2 moles, more preferably 1.2–1.9 moles to 1 mole of molybdenum atom in (a) the hexavalent molybdenum compound, in order to efficiently carry out the reaction.

Provided that, when the composition of X's in the general formula (1) is oxygen-rich, the resulting product shows poor lubricity, and when the composition of X's is sulfur-rich, the resulting product shows stronger corrosive action, thus when the composition of the total of all X's is given as $S_mO_n$ (m+n=4), it is preferable to control m and n to satisfy the range of $1.0 \leq m \leq 3.5$, preferably $1.7 \leq m \leq 3.5$, more preferably $1.8 \leq m \leq 3.0$ (accordingly $3.0 \geq n \geq 0.5$, preferably $2.3 \geq n \geq 0.5$, more preferably $2.2 \geq n \geq 1.0$).

The reaction between (a) a hexavalent molybdenum compound and (b) an alkali hydrogensulfide etc. is carried out in the presence of water in the system. The point is that the reaction system contains water and, for example, at least either of the components (a) or (b) which may be mixed in as an aqueous solution or suspension with the other, or when both of the components are mixed in as solids then water may be added before or after the reaction to make an aqueous solution or suspension. This reaction can be almost completed at room temperature to 60° C. for about 30–60 minutes. By this reaction, an aqueous solution or suspension and the like can be obtained.

Also, in the step of preparing the aqueous suspension and the like, an organic solvent may be added prior to, during, or after the reaction between (a) and (b), in such an amount that does not inhibit the reaction. The organic solvent to be used for such a purpose is not particularly limited, and it may be an aliphatic, alicyclic, aromatic and heterocyclic compound, or a mixture thereof. Examples of such an organic compound include alkanes such as pentane, hexane, heptane, cyclopentane, cyclohexane, ligroin and petroleum ether; alcohols such as methanol, ethanol, propanol, 2-propanol, butanol, 2-butanol, pentanol, hexanol, heptanol, octanol, 2-ethyl hexanol; alkyl ethers such as dimethyl ether, ethyl methyl ether, diethyl ether, methyl isobutyl ether, and ethyl isopropyl ether: ketones such as acetone, ethyl methyl ketone, methyl isobutyl ketone, aromatic compounds such as benzene, toluene, xylene and ethyl benzene; and methylene chloride, chloroform, carbon tetrachloride, pyridine, piperidine, morpholine, pyrimidine, tetrahydrofuran, dioxane, dimethyl sulfoxide, dimethyl formamide, dimethyl acetoamide, hexamethylene phosphoamide and the like. Among these, from the viewpoint of dispersibility of the reaction product and the handling of the solvent, alcohols such as methanol, ethanol, propanol and 2-propanol, ketones such as acetone, ethyl methyl ketone, methyl isobutyl ketone, and aromatic compounds such as benzene, toluene and xylene are preferable.

The organic solvent can be added to the system in any step after the reaction between (a) and (b) to obtain [A] and before the completion of the reaction to obtain MoDTC. Addition of the organic solvent is preferable to efficiently remove by-products and impurities contained in MoDTC, the end-product.

Carbon disulfide, which is the component [B] according to the process of the present invention is a compound represented by the chemical formula $CS_2$ and those which have been conventionally used for experiments or industrial application can be used.

The secondary amine, which is the component [C] according to the process of the present invention can be a secondary amine replaced by a hydrocarbyl group, and the hydrocarbyl group may be saturated or unsaturated, may have a chain structure (straight chain or branched chain) or a ring structure, and may be the same or different. The hydrocarbyl group may contain an ether bond, ester bond and carbonyl bond having oxygen. That is, the hyrocarbyl group selected here makes $R^1$-$R^4$ in MoDTC, the end-product. Such hydrocarbyl groups can be aliphatic, alicyclic, or aromatic. Typical examples of such hydrocarbyl groups include alkyl groups such as ethyl, methyl, propyl, isopropyl, butyl, isobutyl, tert-butyl, pentyl, isopentyl, neopentyl, tert-pentyl, hexyl, heptyl, octyl, 2-ethylhexyl, nonyl, decyl, undecyl, dodecyl, tridecyl, isotridecyl, myristyl, palmityl, and stearyl; alkenyl groups such as propenyl, butenyl, isobutenyl, pentenyl, hexenyl, octenyl, 2-ethylhexenyl, and oleyl; cycloalkyl groups such as cyclopentyl, cyclohexyl, cycloheptyl, methylcyclohexyl and ethylcyclopentyl; aryl groups such as phenyl, toluyl, xylyl, cumenyl, mesityl, α-naphtyl, β-naphtyl, and aralkyl groups such as benzyl and phenethyl. Among these, preferably used are alkyl groups such as ethyl, propyl, isopropyl, butyl, isobutyl, tert-butyl, pentyl, iso-pentyl, neopentyl, tert-pentyl, hexyl, heptyl, octyl, 2-ethylhexyl, nonyl, decyl, undecyl, dodecyl, tridecyl, isotridecyl, myristyl, palmityl and stearyl, and more preferably used are alkyl groups having 4–18 carbon atoms, and the most preferably used are branched-chain alkyl groups having 8–13 carbon atoms. The preferable number of carbon atoms depends on the use. For example, when it is used as an additive for a lubricating oil, a branched-chain alkyl group having 8–13 carbon atoms is preferable from the view point of solubility, and when it is used as an additive for greases, an alkyl group having 3–8 carbon atoms is preferable for the view point of the dispersibility and the molybdenum concentration in MoDTC. Two or more kinds of secondary amines having different hydrocarbyl groups can be used as well.

According to the production process of the present invention, MoDTC having such a hydrocarbyl group that is appropriate for the use application and the working conditions can be produced by selecting an appropriate [C] secondary amine. For example, only one kind of secondary amine having the same hydrocarbyl group is used, MoDTC wherein all of $R^1$–$R^4$ comprise the same hydrocarbyl group can be obtained, and when only one kind of secondary amine having different hydrocarbyl groups is used, in the resulting MoDTC, $R^1$ and $R^3$ are the same and $R^2$ and $R^4$ are the same, however, $R^1$ and $R^3$, are different from $R^2$ and $R^4$, and when two kinds of secondary amines having the same hydrocarbyl group are used, $R^1$ and $R^2$ are the same, and $R^3$ and $R^4$ are the same, however, $R^1$ and $R^2$ are different from $R^3$ and $R^4$ in the resulting MoDTC.

The mineral acid, which is the component [D] in the process of the present invention, can be a monobasic acid, a dibasic acid, a tribasic acid or a partially neutralized acid thereof. Concrete examples thereof include hydrochloric acid, nitric acid, nitrous acid, sulfuric acid, sulfurous acid, phosphoric acid, phosphorous acid, perchloric acid, chloric acid, chlorous acid, hypochlorous acid and the like, but from the view point of reaction efficiency and the purity of the resulting product, hydrochloric acid, nitric acid and sulfuric acid are preferable Furthermore, non-volatile acids are preferable since they are easy to handle, and sulfuric acid is particularly preferable.

The reducing agent, which is the component [E] according to the process of the present invention, is a compound which has the property of giving an electron to other substances, and it is not particularly limited as far as it is a substance which can reduce (a) a hexavalent molybdenum compound to molybdenum which has the skeletal structure of general formula (1). It can be used alone or two or more kinds of reducing agents can be used together. Concrete examples of [E] the reducing agent include hydrides such as hydrogen iodide, hydrogen sulfide, lithium aluminum hydride, and sodium borohydride, salts of lower oxyacids typical examples of which include carbon monoxide, sulfur dioxide, sodium sulfite, sodium dithionate, sodium dithionite (hydrosulfite), sodium hydrogensulfite, sodium pyrosulfite, and sodium thiosulfate, sulfur compounds such as sodium sulfide, sodium polysulfide, and ammonium sulfide, amalgam of a highly electropositive metal such as alkali metal, magnesium, calcium, aluminum and zinc, salts of a metal which is in the low valence state such as iron (II), tin (II), titanium (III), and chromium (II), hydrazine, borane, diborane and aldehydes such as formaldehyde, and acetoaldehyde, saccharides, formic acid, oxalic acid, ascorbic acid, hydrogen peroxide and the like. Among them, hydrides, alkali or alkaline earth metal salts of lower oxyacids, sulfur compounds, reducing sugars, aldehydes, and reducing acids are preferable and from the view point of easy handling and easy availability, particularly preferable are alkali metal salts or alkaline earth metal salts of lower oxyacids such as sodium sulfite and sodium dithionite (hydrosulfite). Carbon disulfide, which is the component [B] shows reducing activity to (a) the hexavalent molybdenum compound existing in the reaction system, however, in order to obtain the molybdenum compound having the skeletal structure of general formula (1) in high yields, the reducing activity of carbon disulfide is not sufficient and [E] the reducing agent must be employed in order to obtain the end-product of high purity in high yields.

As for the blending ratio of [E] the reducing agent, it is preferably added in an amount of 0.01–4 moles, more preferably in an amount of 0.05–2 moles to 1 of molybdenum atom in component [A]. It is not impossible to carry out the production even when the amount of the reducing agent is beyond this range, however, when the blending ratio is much less than 0.01 mole, the molybdenum compound having the skeletal structure of general formula (1) cannot be obtained efficiently, and when it is added in a large amount, the purification step after the reaction becomes complicated and the amount of the by-product is increased.

According to the process of the present invention, the reaction order of above-mentioned components [A], [B], [C], [D], and [E] does not matter. However, in order to improve the yields and inhibit the production of by-products, it is preferable to add the components [B] and [C] at the same time. That means, either components [B] and [C] are added to component [A] at the same time and then component [D] is added thereto, or component [D] is added to the component [A] and then the components [B] and [C] are added thereto at the same time. Component [E] is preferably added during or after the reaction between (a) a hexavalent molybdenum compound and (b) an alkali hydrogensulfide etc.

According to the process of the present invention, the blending ratios of components [B] and [C] are independently 0.9–2 moles, preferably 1–1.5 moles to 1 of the hexavalent molybdenum in component [A], in order to improve the reaction efficiency and the purity of the product, and to decrease the amount of the by-products.

When the alkali equivalent existing in component [A], that is the equivalent weight of (b) an alkali hydrogensulfide and the like, is defined as 1, d which is the equivalent weight of component [D] to be added, can satisfy the following equation (2), when R', which is the total number of carbon atoms contained in $R^1$, $R^2$, $R^3$ and $R^4$, is less than 32;

$$1-[(R'/4)+1] \ [\times 1/10 \leq d \leq 1 \tag{2}$$

and when R' is equal to or more than 32, d can satisfy the following equation (3);

$$0.1 \leq d \leq 10/[(R'/4)+2] \tag{3}$$

and such a blending ratio is preferable. When the blending ratio of [D] exceeds this range, the amount of the by-product is increased, and when it is less than this range, the yields of the product tend to be decreased.

As for the reaction conditions of the above-mentioned components [A], [B], [C], [D] and [E] according to the process of the present invention, the reaction temperature can be near room temperature, however it is preferably 40°–140° C., more preferably 60°–110° C. When the reaction temperature is too high, the amount of the by-products is increased, and when it is too low, the yield of the product is decreased.

The resulting MoDTC is granular or a liquid of high viscosity.

If necessary, the end-product can be washed with water or an organic solvent in order to remove non-reacted raw materials or by-products. When the resulting MoDTC is a powder or solid, it can be refined by slurrying with an organic solvent, and MoDTC having such a particle size that is preferable as an additive for grease can be obtained. As the organic solvent, those organic solvents mentioned above can be used.

According to the process of the present invention, MoDTC having the skeletal structure of general formula (1) which is particularly superior as an additive for a lubricant to other MoDTCs produced by the conventional production process wherein no reducing agent is used, can be efficiently produced industrially. Containing little impurities, MoDTC obtained according to the process of the present invention does not cause corrosion, and shows excellent lubricity when added to a base grease or a base oil for a lubricating oil. According to the present invention, excellent MoDTC can be obtained since the blending ratios of component [A], [B], [C], [D], and [E] are optimized. MoDTC obtained according to the process of the present invention shows good friction decreasing capacity as well as good anti-oxidant action.

When MoDTC obtained according to the process of the present invention is used as an additive for a lubricating oil, it may be added in an amount of 0.01–5 percent by weight, preferably 0.05–1 percent by weight, more preferably 0.1–0.5 percent by weight to a base oil for the lubricating oil, and when it is used as an additive for grease, it may be added in an amount of 0.1–10 percent by weight, preferably 0.5–7 percent by weight, more preferably 1–5 percent by weight to the base grease.

The base oil to be used is not particularly limited as far as it is a conventionally used base oil for the lubricating oil, and illustrative examples include paraffinic oil or naphthenic oil which is separated from natural crude oil and distilled and purified, or a mineral oil obtained by hydrogenation of these, followed by purification with a solvent, HVI oil, or a chemically synthesized oil such as a poly-α-olefin, polyisobutylene (polybutene), diester, polyol ester, phosphoric ester, silicic ester, polyalkylene glycol, polyphenyl ether, silicone, fluorinated compound and alkyl benzene and the like.

When it is used for grease, the base grease is not particularly limited, however, illustrative examples include a metallic soap grease, a metallic soap complex grease, urea-based grease or a grease using organically treated clay (e.g. bentone grease), in which a mineral oil and/or a synthesized oil is used.

To the lubricant composition wherein MoDTC obtained according to the process of the present invention is added to a base grease or a base oil for a lubricating oil, can be added a conventionally known additive for a lubricant. Accordingly an additive such as zinc dithiophosphate, a phenolic antioxidant, an amine based antioxidant, a cleaning agent, a dispersing agent, a viscosity index improver, a pour point depressant, a rust preventive, and another molybdenum based additive can be added in an appropriate manner. When it is used for grease, a solid lubricant such as molybdenum disulfide, graphite and ethylene tetrafluoride etc. can be used together as well. Among them, zinc dithiophosphate is excellent in both anti-oxidant action and friction decreasing capacity, thus it may preferably be used together with MoDTC obtained according to the process of the present invention.

The lubricant composition containing MoDTC obtained according to the process of the present invention can be used as a lubricating oil for internal combustion engines including engines for wheeled vehicles including automobiles, two-cycle engines, aeroplane engines, marine engines, locomotive engines (these engines may be gasoline engines, Diesel engines, gas engines or turbine engines), as automatic transmission fluid, trunk shaft lubricant, gear lubricant, metal working lubricant, grease for automobiles including grease for constant-velocity joints, and industrial grease.

EXAMPLES

The present invention will be illustrated by the following Examples and Comparative Examples. However, it is to be understood that the invention is not intended to be limited by those examples.

Example 1

Into a reaction vessel, 216 ml of water was added and 144 g of molybdenum trioxide were suspended therein as (a) hexavalent molybdenum compound, and then 202 g of 40 wt %-aqueous soda hydrogensulfide solution was added dropwise as (b) alkali hydrogensulfide and reaction was carried out at 40° C. for 1 hour. Subsequently, 34 g of 85 wt %-sodium dithionite was added as [E] reducing agent, and reaction was carried out at 60° C. for 1 hour. Then 324 g of methanol was added thereto, and 254 g of di-2-ethyl hexyl amine as [C] secondary amine as well as 80 g of [B] carbon disulfide were added, then 50.5 g of 35%-sulfuric acid was added as [D] mineral acid to neutralize the reaction mixture and reaction was further carried out at 72° C. for 5 hours.

After completion of the reaction, the mixture was cooled to room temperature and water-methanol layer was removed to give a brown oily matter, which was washed with 500 ml of water three times, then with 500 ml of ethanol, the resulting brown oily matter was dried under reduced pressure to give 425 g of a yellow solid having a melting point of 84°–87° C. (92% yield).

As for the composition of the total of all X's in the compound of general formula (4) obtained in Example 1, S=2.2 and O=1.8. According to the elemental analysis, measured value was Mo: 20.8%, S:21.1%, and N:3.0%. The calculated value was Mo: 20.8%, S:21.5% and N:3.0%.

The blending ratio of each raw material used in Example 1 in terms of molar ratio was as follows:

(a):[B]:[C]:[E]=1:1.05:1.05:0.17

Also (a):(b)=1:1.44 and the value of d, the equivalent weight of component [D] to be added, based on the alkali equivalent of component [A] was 0.25.

In order to identify the structure of MoDTC in the above-mentioned reaction product, which corresponds to the compound of general formula (4), the following procedure was carried out. That is, the reaction product was dissolved in diethyl ether and re-crystallized from cyclohexane, filtered and the solvent was removed, then the crystal was dried under reduced pressure to give a yellow crystal.

The obtained yellow crystal was identified as the compound of general formula (4) by infrared absorption spectrum (IR), proton nuclear magnetic resonance spectrum (H-NMR), gel permeation chromatography (GPC), silica gel thin-layer chromatography (TLC) and X-ray diffraction analysis. Then this compound was used together with dioctyl phthalate as an internal standard substance and a standard curve was prepared by high performance liquid chromatography (HPLC). The standard curve was used for measuring the purity of the compound of general formula (4) in the yellow solid obtained in Example 1, and it was found to be 98.7%.

Comparative Example 1

A process analogous to that of Example 1 was repeated except that sodium dithionite was not used, to give a brown oily matter. It was washed and dried in a manner similar to that of Example 1 to give 405 g of a sticky brown semi-solid having a melting point of 76°–80° C. The yield was 88%.

The above-mentioned brown sticky semi-solid (200 g) was washed with butanol twice by heating, then washed with ethyl alcohol once, then dried under reduced pressure to give 182 g of a yellowish brown solid having a melting point of 78°–84° C.

The yellowish solid compound was subjected to IR, H-NMR, GPC and elemental analysis to give nearly the same results as those of the compound obtained in Example 1. However, under TLC more spots were detected from this compound than the compound of Example 1, to confirm that there were a lot of by-products existing in this compound. The purity measured by HPLC was 76.9%, which showed there were a lot of impurities.

Comparative Example 2

A procedure analogous to that of Example 1 was carried out, provided that the system was controlled to pH 10 with 20%-aqueous sodium hydroxide solution instead of adding sodium dithionite, and the reaction was completed without neutralization by sulfuric acid after di-2-ethyl hexyl amine and carbon disulfide were added. The product was washed and dried in a manner similar to that of Example 1, to give 245 g of a yellow solid having a melting point of 80°–84° C. The yield was a low 53%.

The yellow solid compound was subjected to IR, H-NMR, GPC and elemental analysis to give nearly the same results as those of the compound obtained in Example 1. However, under TLC more spots were detected from this compound than the compound of Example 1, to confirm that there were a lot of by-products existing in this compound. The purity measured by HPLC was 80.5 which showed there were a lot of impurities.

Examples 2–14 and Comparative Examples 3–6

Procedures analogous to that of Example 1 are carried out, where the kind and amount of reducing agents, and acids for neutralization were changed as shown in Table 1. The yield (weight and percentage) of each compound obtained according to those processes, and the purities of the compounds of general formula (4) measured by HPLC are also shown in Table 1. IR, H-NMR, GPC, TLC and elemental analysis of these compounds gave almost the same results as those of the compound obtained in Example 1.

It is clear from the Table 1 that the yields and the purities of the compounds obtained in Comparative Examples 3–6 were inferior to those of the compounds obtained in the Examples.

As for the composition of the total of all X's in the compound of general formula (4) obtained in Example 15, S=2.1 and 0=1.9. The structure of the compound was identified by IR, H-NMR, GPC, TLC and elemental analysis. According to the elemental analysis, measured value was Mo: 18.0%, S:18.2%, and N:2.7%. The calculated value was Mo: 18.4%, S:18.7% and N:2.7%. The purity measured by HPLC in a manner similar to that of Example 1 was 97.3%.

The blending ratio of each raw material used in Example 15 in terms of molar ratio was as follows:

(a):[B]:[C]:[E]=1:1.05:1.05:0.5

TABLE 1

| No | Name of [E] reducing agents | Amount of [E] used (g) | Value of Mo:[E] | Name of [D] mineral acids | Amount of [E] used (g) | Value of(d) | Product attribute | Melting point °C. | Yield (g) | (%) | Purity (%) |
|---|---|---|---|---|---|---|---|---|---|---|---|
| Examples | | | | | | | | | | | |
| 2 | formalin (37%) | 41 | 0.51 | hydrochloric acid (20%) | 65.8 | 0.25 | yellow solid | 84–87 | 413 | 90 | 97.1 |
| 3 | ascorbic acid | 32 | 0.18 | hydrochloric acid (20%) | 65.8 | 0.25 | yellow solid | 84–87 | 415 | 90 | 97.5 |
| 4 | sodium hydrogensulfite | 52 | 0.50 | hydrochloric acid (20%) | 65.8 | 0.25 | yellow solid | 84–87 | 418 | 91 | 99.1 |
| 5 | sodium thiosulfate | 79 | 0.50 | phosphoric acid | 40 | 0.85 | yellow solid | 84–87 | 424 | 92 | 91.7 |
| 6 | sodium sulfite | 63 | 0.50 | sulfuric acid (35%) | 90.9 | 0.45 | yellow solid | 84–87 | 421 | 91 | 97.4 |
| 7 | potassium sulfite | 79 | 0.50 | sulfuric acid (35%) | 90.9 | 0.45 | yellow solid | 84–87 | 413 | 90 | 99.1 |
| 8 | sodium sulfite | 24 | 0.19 | sulfuric acid (35%) | 90.9 | 0.45 | yellow solid | 84–87 | 419 | 91 | 99.2 |
| 9 | sodium sulfite | 189 | 1.50 | sulfuric acid (35%) | 90.9 | 0.45 | yellow solid | 84–87 | 423 | 92 | 95.1 |
| 10 | sodium sulfite | 400 | 3.17 | sulfuric acid (35%) | 90.9 | 0.45 | yellow solid | 84–87 | 437 | 95 | 91.5 |
| 11 | sodium dithionite (85%) | 10.2 | 0.05 | sulfuric acid (35%) | 90.9 | 0.45 | yellow solid | 84–87 | 411 | 89 | 95.8 |
| 12 | sodium sulfite sodium dithionite (85%) | 12.6 20.5 | 0.10 0.10 | sulfuric acid (35%) | 90.9 | 0.45 | yellow solid | 84–87 | 420 | 91 | 99.1 |
| 13 | sodium sulfite | 24 | 0.19 | sulfuric acid (35%) | 30.2 | 0.15 | yellow solid | 84–87 | 402 | 87 | 99.0 |
| 14 | sodium sulfite | 24 | 0.19 | sulfuric acid (35%) | 121 | 0.6 | yellow solid | 83–86 | 429 | 93 | 95.3 |
| Comparative Examples | | | | | | | | | | | |
| 3 | sodium dithionite (85%) | 1.02 | 0.005 | sulfuric acid (35%) | 90.9 | 0.45 | brown solid | 80–84 | 422 | 92 | 81.3 |
| 4 | sodium sulfite | 600 | 4.76 | sulfuric acid (35%) | 90.9 | 0.45 | brown solid | 78–81 | 451 | 98 | 79.8 |
| 5 | sodium dithionite (85%) | 40.8 | 0.20 | sulfuric acid (35%) | 252 | 1.25 | dark brown viscous semi-solid | | 455 | 99 | 62.4 |
| 6 | sodium dithionite (85%) | 40.8 | 0.20 | sulfuric acid (35%) | 10.1 | 0.05 | brown solid | 78–82 | 308 | 67 | 83.2 |

Example 15

Into a reaction vessel, 300 ml of water was added and 144 g of molybdenum trioxide were suspended therein, and 202 g of 40 wt %-aqueous soda hydrogensulfide solution was added dropwise and reaction was carried out at 40° C. for 1 hour. Subsequently, 63 g of anhydrous sodium sulfite was added, and reaction was carried out at 60° C. for 1 hour. Then 500 g of 2-propanal was added thereto, and 27 g of di-2-ethyl hexyl amine, 201 g of diisotridecyl amine and 80 g of carbon disulfide were added, then 91 g of 35%-sulfuric acid was added to neutralize the reaction mixture and reaction was further carried out at 72° C. for 5 hours.

After completion of the reaction, the mixture was cooled to room temperature and water-2-propanol layer was removed to give a brown oily matter, which was washed with 500 ml of water three times, then with 500 ml of ethanol, and the resulting brown oily matter was dried under reduced pressure to give 475 g of a brown viscous semi-solid (89% yield).

Also (a):(b)=1:1.44 and the value of d, the equivalent weight of component [D] to be added, based on the alkali equivalent of component [A] was 0.45.

Comparative Example 7

A process analogous to that of Example 15 was carried out except that anhydrous sodium sulfite was not used, to give a brown viscous semi-solid (392 g, yield 74%).

IR, H-NMR, GPC and elemental analysis of the compound gave almost the same results as those of the compound obtained in Example 15, however, by TLC, more spots were detected from this compound than the compound of Example 15, to confirm that there were a lot of by-products existing in this compound. The purity measured by HPLC was 69.9%, which showed there were a lot of impurities.

Example 16

Into a reaction vessel, 500 ml of water was added and 300 ml of toluene, 242 g of sodium molybdate dihydrate and 300 g of potassium sulfide nonahydrate were added thereto, then 197 g of 35%-sulfuric acid was added with stirring and reaction was carried out at 60° C. for 2 hours. Subsequently, 129 g of di-n-butyl amine and 77 g of carbon disulfide were added thereto and 79 g of sodium thiosulfate was added and reaction was carried out at 60° for 6 hours. After completion of the reaction, the precipitate was filtered out and washed with warm water of 40° C. three times, then washed with 2-propanol, and dried to give 302 g of a yellowish brown solid (87%).

As for the composition of the total of all X's in the compound of general formula (4) obtained in Example 16, S=2.3, O=1.7. The structure of the compound was identified by IR, H-NMR, GPC, TLC and elemental analysis. According to the elemental analysis, measured value was Mo: 27.5%, S:28.6% and N:4.0%. The calculated value was Mo: 27.4%, S:28.8% and N:4.0%. The purity measured by HPLC in a manner similar to that of Example 1 was 99.1%.

The blending ratio of each raw material used in Example 16 in terms of molar ratio was as follows;

(a):[B]:[C]:[E]=1:1.00:1.01:0.50

Also (a):(b)=1:1.10 and the value of d, the equivalent weight of component [D] to be added, based on the alkali equivalent of component [A] was 0.64.

Comparative Example 8

A process analogous to that of Example 16 was carried out except that sodium thiosulfate was not used to give a brown viscous semi-solid (252 g, yield 72%).

IR, H-NMR, GPC and elemental analysis of the compound gave almost the same results as those of the compound obtained in Example 16. However, under TLC more spots were detected from this compound than the compound of Example 16, to confirm that there were a lot of by-products existing in this compound. The purity measured by HPLC was 65.5%, which showed there were a lot of impurities.

Example 17

Into a reaction vessel, 216 ml of water was added and 144 g of molybdenum trioxide were suspended therein, then 202 g of 40 wt %-aqueous soda hydrogensulfide solution was added dropwise and reaction was carried out at 40° C. for 1 hour. Subsequently, 34 g of 85 wt %-sodium dithionite was added and reaction was carried out at 60° C. for 1 hour. Then 50.5 g of 35%-sulfuric acid was added to neutralize the reaction mixture and reaction was carried out for 1 hour, and 324 g of 1-butanol was added thereto. Dithiocarbamic acid which was prepared in a separate reaction vessel by reacting 254 g of di-2-ethyl hexyl amine with 80 g of carbon disulfide, was added dropwise and reaction was further carried out at 70° C. for 6 hours. After completion of the reaction, the mixture was cooled to room temperature and water-1-butanol layer was removed to give a brown oily matter, which was washed with 500 ml of water three times, then with 500 ml of ethanol, the resulting brown oily matter was dried under reduced pressure to give 411 g of a yellow solid having a melting point of 84°–87° C. (89% yield).

IR, H-NMR, GPC, TLC and elemental analysis of the compound gave almost the same results as those of the compound obtained in Example 1. The purity measured by HPLC was 94.4%.

The blending ratio of each raw material used in Example 17 in terms of molar ratio was as follows:

(a):[B]:[C]:[E]=1:1.05:1.05:0.17

Also (a):(b)=1:1.44 and the value of d based on the alkali equivalent of component [A] was 0.25.

Application Example 1

The compounds obtained in Examples 1, 15 and 17 as well as the compounds obtained in Comparative Examples 1, 2 and 7 were subjected to the following tests. The results are shown in Table 2.

1) Copper plate corrosion test

Each compound (3 parts by weight) was dissolved in 99 parts by weight of dioctyl phthalate by heating and subjected to copper plate corrosion test (JIS K2513). The test conditions was carried out at 100° C. for 3 hours.

2) Load test

Each compound (0.15 parts by weight) was dissolved in 100 parts by weight of 150-neutral oil and the seizing load was measured by a high speed four ball type friction tester (produced by Shinko Engineering Co., Ltd.). The measuring conditions were; speed: 1500 rpm. test time:1 minute, and test temperature: room temperature.

3) Friction test

Each compound (0.15 parts by weight) was dissolved in 100 parts by weight of 150-neutral oil and the friction coefficient was measured by a SRV dynamic friction test machine (produced by Optimol Co., Ltd.).

As for the test conditions, load was 200N, vibration frequency was 50 Hz, amplitude was 1 mm, temperature was 80° C., and the test time was 15 min. Test was carried out by line contact; φ15×22 mm for the upper test chip, and φ24×6.85 mm for the lower test chip.

Each compound (0.15 parts by weight) and 1 part by weight of zinc dialkyl dithiophosphate (ZDTP) which was synthesized by the use of 2-ethyl hexanol were dissolved in 100 parts by weight of 150-neutral oil and subjected to the test with the SRV dynamic friction test machine in a similar manner to measure the friction coefficient.

TABLE 2

| | Copper Plate Corrosion Test | High Speed Four Ball Type Friction Test Seizing Load (kg) | SRV Dynamic Friction Test Friction Coefficient | |
|---|---|---|---|---|
| | | | MoDTC | MoDTC + ZDTP |
| Example 1 | 2 | 141 | 0.062 | 0.052 |
| Example 15 | 2 | 141 | 0.063 | 0.050 |
| Example 17 | 2 | 141 | 0.062 | 0.051 |
| Comp. Example 1 | 4 | 141 | 0.083 | 0.071 |
| Comp. Example 2 | 3 | 141 | 0.079 | 0.066 |
| Comp. Example 7 | 4 | 141 | 0.085 | 0.080 |
| Base Oil | 1 | 79 | 0.150 | 0.146 |

Application Example 2

The compound obtained in Example 16, and the compound obtained in Comparative Example 8 were subjected to the following tests. The results are shown in Table 3.

1) Copper plate corrosion test

Each compound (3 parts by weight) was dissolved in 99 parts by weight of dioctyl phthalate by heating and subjected to a copper plate corrosion test (JIS K2513). The test conditions was carried out at 100° C. for 3 hours.

2) Friction test

Each compound (3 parts by weight) was dispersed in 100 parts by weight of urea grease and the friction coefficient was measured by a SRV dynamic friction test machine (produced by Optimol Co., Ltd.).

As for the test conditions, load was 200N, vibration frequency was 50 Hz, amplitude was 1 mm, temperature was 80° C., and the test time was 15 min. Test was carried out by a $\phi$10 mm ball for the upper test chip, and by point contact of $\phi$24×6.85 mm for the lower test chip.

Each compound (3 parts by weight) and 3 parts by weight of ZDTP which was synthesized by the use of 2-ethyl hexanol were dispersed in 100 parts by weight of urea grease and subjected to the test with the SRV dynamic friction test machine in the similar manner to measure the friction coefficient.

TABLE 3

| | Copper Plate Corrosion Test | SVR Dynamic Friction Test (Friction Coefficient) | |
|---|---|---|---|
| | | MoDTC | MoDTC + ZDTP |
| Example 16 | 2 | 0.091 | 0.054 |
| Comp. Example 8 | 3 | 0.093 | 0.073 |
| Base Grease | 1 | 0.135 | 0.130 |

As is clear from Tables 2 and 3, MoDTC produced by the process of the present invention has superior results than those produced in the Comparative Examples in the copper plate corrosion test.

Although the seizing loads were nearly the same, it is clear that MoDTC obtained according to the process of the present invention is superior in lubricity when added to both the lubricating oil and the grease.

According to the present invention, molybdenum oxysulfide dithiocarbamate (MoDTC) can be produced efficiently in high yields, and the obtained MoDTC shows little corrosive action, as well as excellent friction characteristics and lubricity. The composition using the MoDTC obtained according to the present invention can be used as a lubricant having little corrosive action and excellent lubricity.

What is claimed is:

1. A process for producing molybdenum oxysulfide dithiocarbamate comprising:

reacting [A] an aqueous solution or suspension prepared by reacting (a) a compound having hexavalent molybdenum, with (b) an alkali hydrogen sulfide or an alkali sulfide;
[B] a carbon disulfide;
[C] a secondary amine;
[D] a mineral acid; and
[E] a reducing agent wherein said reducing agent, [E], is other than the compound used as [A] (b) and is added and reacted at any stage of said process.

2. The process according to claim 1, wherein the blending ratio of components [A], [B], [C] and [D] are such that the amount of component [B] is 0.9–2 moles, that of component [C] is 0.9–2 moles to 1 mole of the hexavalent molybdenum atom contained in component [A], and that d, which is the equivalent weight of component [D] to be added when the alkali equivalent of component [A] is defined as 1, is within the range satisfying the following equation (2), when R' is less than 32, $$1-[(R'/4)+1]\times 1/10 \leq d \leq 1 \quad (2)$$

and d is within the range satisfying the following equation (3) when R' is equal to or more than 32, $$0.1 \leq d \leq 10/[(R'/4)+2] \quad (3)$$

(wherein R' is the total number of carbon atoms contained in $R^1$, $R^2$, $R^3$ and $R^4$).

3. The process according to claim 1, wherein (b) the alkali hydrogensulfide or alkali sulfide of 0.01–4 moles is reacted with 1 mole of molybdenum atom contained in (a) the compound having hexavalent molybdenum.

4. The process according to claim 1, wherein the blending ratio of [E] the reducing agent is 0.01–4 moles to 1 of the molybdenum atom contained in [A].

5. The production process according to claim 1, wherein [E] the reducing agent is added during and/or after the reaction between (a) the compound having hexavalent molybdenum and (b) the alkali hydrogensulfide or alkali sulfide.

6. The process according to claim 1, wherein $1.0 \leq m \leq 3.5$, when the composition of the total of all X's in the general formula (1) is given as $S_mO_n$.

7. A lubricant composition comprising molybdenum oxysulfide dithiocarbamate which is produced by the process according to claim 1.

8. A lubricant composition comprising zinc dithiophosphate and molybdenum oxysulfide dithiocarbamate which is produced by the process according to any of claim 1.

9. The process according to claim 1, wherein said reducing agent, [E], is a hydride.

10. The process according to claim 1, wherein said reducing agent, [E], is an alkali metal salt or an alkaline earth metal salt of dithionous acid, sulfurous acid or thiosulfuric acid.

11. The process according to claim 1, wherein said reducing agent, [E], is a sulfur compound.

12. The process according to claim 1, wherein said reducing agent, [E], is a reducing sugar.

13. The process according to claim 1, wherein said reducing agent, [E], is an aldehyde.

14. The process according to claim 1, wherein said reducing agent, [E], is a reducing acid.

* * * * *